United States Patent [19]

Wietfeld

[11] Patent Number: 5,055,595

[45] Date of Patent: Oct. 8, 1991

[54] ETHERIFIED FLUORESCEIN COMPOUNDS

[75] Inventor: Bernhard Wietfeld, Efringen-Kirchen, Fed. Rep. of Germany

[73] Assignee: Ciba-Geigy Corporation, Ardsley, N.Y.

[21] Appl. No.: 435,876

[22] Filed: Nov. 14, 1989

[30] Foreign Application Priority Data

Nov. 17, 1988 [CH] Switzerland .......................... 4259/88

[51] Int. Cl.$^5$ ............................................ C07D 493/10
[52] U.S. Cl. ...................................... 549/224; 503/221
[58] Field of Search .......................... 549/224; 503/221

[56] References Cited

U.S. PATENT DOCUMENTS 4,800,148 1/1989 Harada et al. ...................... 430/138
4,880,730 11/1989 Sato et al. ............................ 430/520

OTHER PUBLICATIONS

Chem. Abstr., 109:29995, Harada et al. (1988).
Sato, Chemical Abstracts, vol. 108 (1988), 177032m.
Sato et al., Chemical Abstracts, vol. 112 (1990), 108413g.
Anzai et al., Chemical Abstracts, vol. 11 (1989), 2444389.

*Primary Examiner*—Richard L. Raymond
*Attorney, Agent, or Firm*—George R. Dohmann; Edward McC. Roberts

[57] ABSTRACT

Etherified fluorescein compounds of the general formula

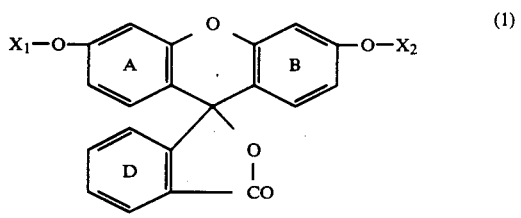

in which $X_1$ is alkyl having 4 to 12 carbon atoms or cycloalkyl and $X_2$ is alkyl which is unsubstituted or substituted by halogen, hydroxyl, cyano or lower alkoxy, or cycloalkyl, the rings A and B, independently of one another, are unsubstituted or substituted by halogen, lower alkyl or lower alkoxy, and the ring D is unsubstituted or substituted by halogen, nitro, lower alkyl, lower alkoxy, lower alkylthio, lower alkoxycarbonyl, amino, mono-lower alkylamino or di-lower alkylamino, with the exception that $X_1$ and $X_2$ are not at the same time n-butyl.

These novel lactone compounds are particularly suitable for use a color formers in pressure-sensitive or heat-sensitive recording materials and they produce intense yellow, orange or rose-pink colorations.

15 Claims, No Drawings

ETHERIFIED FLUORESCEIN COMPOUNDS

The present invention relates to novel etherified fluorescein compounds, to a process for their preparation and to their use as colour formers in recording materials.

The etherified fluorescein compounds according to the invention have the general formula

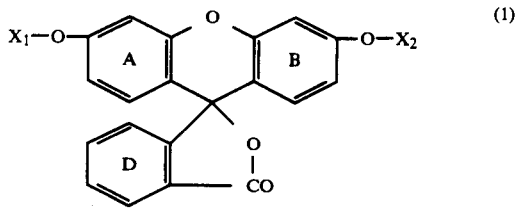

(1)

in which $X_1$ is alkyl having 4 to 12 carbon atoms or $C_5$–$C_6$cycloalkyl and $X_2$ is alkyl having 1 to 12 carbon atoms, which is unsubstituted or substituted by halogen, hydroxyl, cyano or lower alkoxy, or $C_5$–$C_6$cycloalkyl, the rings A and B, independently of one another, are unsubstituted or substituted by halogen, lower alkyl or lower alkoxy, and the ring D is unsubstituted or substituted by halogen, nitro, lower alkyl, lower alkoxy, lower alkylthio, lower alkoxycarbonyl, amino, monolower alkylamino or di-lower alkylamino, with the exception that $X_1$ and $X_2$ are not at the same time n-butyl.

In the definition of the radicals of the lactone compounds, lower alkyl, lower alkoxy and lower alkylthio are groups or constituents of groups containing 1 to 5, in particular 1 to 3, carbon atoms.

Examples of groups of this type are methyl, ethyl, n-propyl, isopropyl, n-butyl, sec-butyl, isobutyl, tert-butyl, amyl, isoamyl or sec-amyl and methoxy, ethoxy, isopropoxy, isobutoxy or tert-butoxy and methylthio, ethylthio, propylthio or butylthio, respectively.

Halogen is, for example, fluorine, bromine or preferably chlorine.

As alkyl radicals, $X_1$ and $X_2$ can be linear or branched. Examples of alkyl radicals of this type are n-butyl, sec-butyl, isobutyl, 1,1,3,3-tetramethylbutyl, amyl, isoamyl, n-hexyl, 2-ethylhexyl, n-heptyl, n-octyl, isooctyl, n-nonyl, isononyl or n-dodecyl. $X_2$ can also be methyl, ethyl, n-propyl or isopropyl.

If the alkyl radical in $X_2$ is substituted, it is cyanoalkyl, halogenoalkyl, hydroxyalkyl or alkoxyalkyl, in each case preferably having a total of 2 to 8 carbon atoms, for example 2-cyanoethyl, 2-chloroethyl, 3-chloroethyl, 2-hydroxyethyl, 3-hydroxypropyl, 2-methoxyethyl, 2-ethoxyethyl or 3-methoxypropyl.

Examples of cycloalkyl as X radicals are cyclopentyl or preferably cyclohexyl.

$X_1$ is preferably n-butyl, isobutyl, sec-butyl, 1,1,3,3-tetramethylbutyl, n-pentyl, isopentyl, n-hexyl or n-octyl. $X_2$ is preferably $C_1$–$C_8$alkyl, 2-cyanoethyl, 2-methoxyethyl or 2-ethoxyethyl and particularly methyl, ethyl, n-propyl, isopropyl, n-butyl, sec-butyl, 1,1,3,3-tetramethylbutyl, isopentyl or n-octyl.

It is advantageous for the rings A and B not to be further substituted. If the rings A and B are substituted, they preferably carry, independently of one another, in each case 1 or 2 halogen atoms.

The ring D can be substituted, in the first place, by halogen, nitro, lower alkyl, lower alkoxycarbonyl or di-lower alkylamino. Preferably the ring D is unsubstituted.

Etherified fluorescein compounds of practical importance have the formula

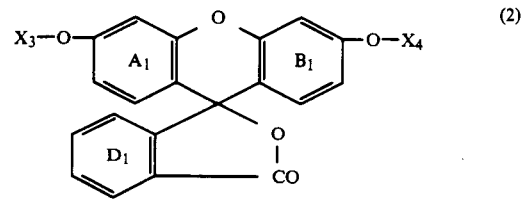

(2)

in which $X_3$ is $C_4$–$C_8$alkyl and $X_4$ is $C_1$–$C_8$alkyl or $C_2$–$C_4$alkyl which is substituted by halogen, cyano or lower alkoxy, and the rings $A_1$, $B_1$ and $D_1$, independently of one another, are unsubstituted or substituted by halogen.

Amongst the lactone compounds of the formula (2), those in which $X_4$ is $C_1$–$C_5$alkyl and the rings $A_1$, $B_1$ and $D_1$ are unsubstituted are particularly preferred.

Etherified fluorescein compounds of particular interest are those of the formula

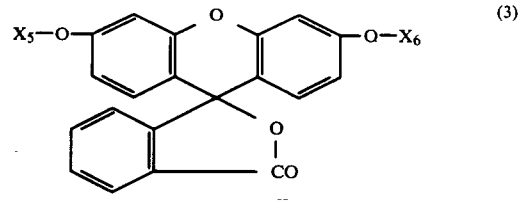

(3)

in which $X_5$ is n-butyl, sec-butyl, isobutyl, n-pentyl, isopentyl, hexyl or n-octyl and $X_6$ is methyl, ethyl, n-propyl, isopropyl, n-butyl, sec-butyl, n-pentyl or isopentyl.

Both in formula (2) and in formula (3), etherified fluorescein compounds in which the X radicals are n-butyl at the same time are excluded.

The etherified fluorescein compounds according to the invention are prepared by etherifying a fluorescein compound of the formula

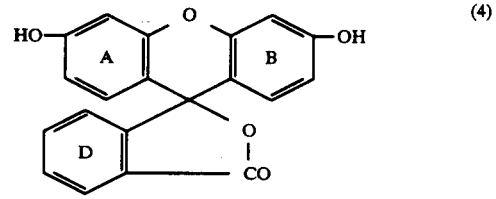

(4)

in which A, B and D are as defined above with an appropriate alkylating agent or cycloalkylating agent.

Etherification is preferably carried out in the presence of an acid-binding agent, for example an alkali metal hydroxide, an alkali metal carbonate or a tertiary nitrogen base, for example pyridine or trialkylamines, and preferably also in the presence of a quaternary ammonium salt, for example tetrabutylammonium bromide, if appropriate in an organic solvent or in an aqueous organic two-phase medium and at reflux temperature.

Examples of suitable solvents are cycloaliphatic or aromatic hydrocarbons, for example cyclohexane, benzene, toluene or xylene; chlorinated hydrocarbons, for example chloroform, ethylene dichloride or chlorobenzenes, especially dichlorobenzene; ethers, for example diethyl ether or glycol dimethyl ether; cyclic ethers, for example dioxane or tetrahydrofuran; and dimethylformamide, diethylformamide, dimethyl sulfoxide, acetone or acetonitrile.

If $X_1$ and $X_2$ are different from one another the etherification with the corresponding alkylating agents is carried out in two stages, in which case $X_1$ and $X_2$ are introduced successively and the intermediates can be isolated if desired. If, on the other hand, $X_1$ and $X_2$ are introduced at the same time, mixtures of the corresponding etherified fluorescein compounds are preferably formed.

Isolation of the end products or of the desired intermediates is effected in a generally known manner by treating the reaction products with suitable, preferably non-polar, organic solvents, for example benzene, chlorobenzene, toluene or xylene, separating the phases formed and removing the solvent from the organic phases. If necessary, the products can be purified by recrystallization, for example from isopropanol.

Suitable alkylating agents are alkyl halides or, in some cases, also dialkyl sulfates, such as dimethyl sulfate or diethyl sulfate, or tosyl esters, such as methyl tosylate or n-butyl tosylate.

Specific examples of the alkyl halides include methyl chloride, methyl bromide, methyl iodide, ethyl chloride, ethyl bromide, ethyl iodide, propyl chloride, isopropyl chloride, propyl bromide, n-butyl bromide, sec-butyl bromide, 1,1,3,3-tetramethylbutyl bromide, amyl bromide, isopentyl bromide, hexyl bromide, heptyl bromide, n-octyl bromide, 2,2-dimethylpropyl bromide, 1-bromo-2-chloropropane, 1-bromo-3-chloropropane, 1-bromo-4-chlorobutane, 1-bromo-5-chloropentane, 2,3-dimethyl-3-bromopentane, 3-ethyl-3-bromopentane or 4-methyl-3-bromoheptane.

Cycloalkylating agents which may be mentioned are, in particular, cyclopentyl chloride, cyclohexyl chloride or cyclohexyl bromide.

The etherified fluorescein compounds of the formulae (1) to (3) are normally colourless, but in some cases are also slightly coloured. When these colour formers are brought into contact with a, preferably acid, developer, i.e. an electron acceptor, they immediately produce, depending on the developer used, intense yellow, orange or rose-pink colour shades which are particularly fast to light and sublimation.

The lactone compounds of the formulae (1) to (3) are also very valuable when mixed with one or more other known colour formers, for example 3,3-(bis-aminophenyl)-phthalides, 3-indolyl-3-aminophenylazaphthalides, (3,3-bis-indolyl)-phthalides, 3-aminofluoranes, 3-dialkylamino-7-dibenzylaminofluoranes, 3-dialkylamino-6-methyl-7-arylaminofluoranes, leucoauramines, spiropyranes, spirodipyranes, chromenoindoles, phenoxazines, phenothiazines, quinazolines, rhodamine lactams, carbazolylmethanes or other triarylmethane leuco dyes, in order to produce grey or black colorations.

The lactone compounds of the formulae (1) to (3) display an excellent colour intensity both on activated clays and on phenolic substrates. They are particularly suitable for use as rapid-developing colour formers for use in a heat-sensitive, or especially a pressure-sensitive, recording material, which can be either a copying material or a recording material. They are distinguished by the fact that they are stable to pH, fast to light and readily soluble in the capsule oils. After exposure to light in a CB sheet they display a slight decrease in colour strength (CB deactivation).

A pressure-sensitive material consists, for example, of at least one pair of sheets containing at least one colour former of the formulae (1) to (3), dissolved in an organic solvent, and an electron acceptor as developer.

Typical examples of such developers are activated clay substances, such as attapulgus clay, acid clay, bentonite, montmorillonite, activated clay, for example acid-activated bentonite or montmorillonite, and also zeolite, halloysite, silicon dioxide, aluminium oxide, aluminium sulfate, aluminium phosphate, zirconium dioxide, zinc chloride, zinc nitrate, activated kaolin or any desired clay. Developers which can be used are also organic compounds having an acid reaction, for example phenols, resorcinols or salicylic acids which are unsubstituted or substituted in the ring, for example 3,5-bis-($\alpha,\alpha$-dimethylbenzyl)-salicylic acid or 3,5-bis-($\alpha$-methylbenzyl)-salicylic acid or salicylic acid esters and metal salts thereof, for example zinc salts, and also a polymeric material having an acid reaction, for example a phenolic polymer, an alkylphenol acetylene resin, a maleic acid/colophony resin or a partly or completely hydrolyzed polymer of maleic anhydride with styrene, ethylene or vinyl methyl ether, or carboxymethylene. It is also possible to employ mixtures of the said monomeric and polymeric compounds. Developers which are particularly preferred are acid-activated bentonite, zinc salicylates or the condensation products of p-substituted phenols with formaldehyde. The latter can also be modified with zinc.

In addition, the developers can also be employed as a mixture with pigments or other assistants which are unreactive per se or of low reactivity, such as silica gel or UV absorbers, for example 2-(2'-hydroxyphenyl)-benzotriazoles. The following are examples of such pigments: talc, titanium dioxide, aluminium oxide, aluminium hydroxide, zinc oxide, chalk, clays, such as kaolin, and also organic pigments, for example urea-formaldehyde condensates (BET surface area 2–75 m$^2$/g) or melamine-formaldehyde condensation products.

At the points where it comes into contact with the electronic acceptor, the colour former gives a coloured marking. In order to prevent premature activation of the colour formers present in the pressure-sensitive recording material, these colour formers are, as a rule, separated from the electron acceptor. This can be achieved advantageously by incorporating the colour formers in foam-like, sponge-like or honeycomb-like structures. The colour formers are preferably enclosed in microcapsules which can as a rule be ruptured by pressure.

When the capsules are ruptured by pressure, for example by means of a pencil, the colour former solution is transferred to an adjacent sheet coated with an electron acceptor, as a result of which a coloured area is produced. The colour results from the dye formed in the course of this, which absorbs within the visible range of the electromagnetic spectrum.

The colour formers are preferably encapsulated in the form of solutions in organic solvents. Examples of suitable solvents are, preferably, non-volatile solvents, for example polyhalogenated paraffin or biphenyl, such as chloroparaffin, monochlorodiphenyl or trichlorodiphenyl, and also tricresyl phosphate, di-n-butyl phthalate, dioctyl phthalate, trichlorobenzene, trichloroethyl phosphate, aromatic ethers, such as benzyl phenyl ether, hydrocarbon oils, such as paraffin or kerosene, for example derivatives of biphenyl, naphthalene or terphenyl which are alkylated by isopropyl, isobutyl, sec-butyl or tert-butyl, dibenzyltoluene, partially hydrogenated terphenyl, mono-$C_1$-$C_3$alkylated or tetra-$C_1$-$C_3$alkylated diphenyl alkanes, dodecylbenzene, benzylated xylenes or other chlorinated or hydrogenated, condensed aromatic hydrocarbons. Mixtures of different solvents, in particular mixtures of paraffin oils or kerosene and diisopropylnaphthalene or partially hydrogenated terphenyl, are often employed in order to obtain optimum solubility for the colour formation, a rapid and intense coloration and a viscosity advantageous for microencapsulation.

The capsule walls can be formed uniformly round the droplets of the colour former solution by coacervation forces, and the encapsulation material is described, for example, in U.S. Pat. No. 2,800,457. The capsules can preferably also be formed from an aminoplast or modified aminoplasts by polycondensation, as described in British Patent Specifications 989,264, 1,156,725, 1,301,052 and 1,355,124. Microcapsules which are formed by interface polymerization, for example capsules formed from polyester, polycarbonate, polysulfonamide, polysulfonate and particularly polyamide or polyurethane, are also suitable.

The microcapsules containing colour formers of the formulae (1) to (3) can be used for the preparation of pressure-sensitive copying materials of a very wide variety of known types. The various systems differ from one another essentially in the arrangement of the capsules and the colour reactants and in the carrier material.

A preferred arrangement is one in which the encapsulated colour former is present in the form of a layer on the reverse side of a transfer sheet and the electron acceptor is present in the form of a layer on the front side of a receiver sheet.

Another arrangement of the constituents consists in the microcapsules containing the colour former and the developer being present in or on the same sheet in the form of one or more individual layers or being present in the paper pulp.

The capsules are preferably fixed to the carrier by means of a suitable binder. Since paper is the preferred carrier material, this binder is mainly a paper coating agent, such as gum arabic, polyvinyl alcohol, hydroxymethylcellulose, casein, methylcellulose, dextrin, starch, starch derivatives or polymer latices. Examples of the latter are butadiene/styrene copolymers or acrylic homopolymers or copolymers.

The paper used is not only normal paper made of cellulose fibres, but also paper in which the cellulose fibres have been replaced (partly or completely) by fibres composed of synthetic polymers.

The compounds of the formulae (1) to (3) can also be used as colour formers in a heat-reactive recording material. This contains, as a rule, at least a substrate, a colour former, an electron acceptor and, if appropriate, also a binder and/or wax. If desired, activators or sensitizers can also be present in the recording material.

Heat-reactive recording systems embrace, for example, heat-sensitive recording and copying materials and recording and copying papers. These systems are used, for example, for recording information, for example in electronic computers, teleprinters, telewriters or in recording instruments and measuring instruments, for example electrocardiographs. The production of an image (marking) can also be carried out manually using a heated pen. Laser beams are a further device for the production of markings by means of heat.

The heat-reactive recording material can be built up in such a way that the colour former is dissolved or dispersed in a layer of binder, and the developer is dissolved or dispersed in the binder in a second layer. Another possible means consists in dispersing both the colour former and the developer in one layer. The binder is softened by heat in specific areas, and at these points at which heat is applied, the colour former comes into contact with the electron acceptor and the desired colour is developed immediately.

Suitable developers are the same electron acceptors as those used in pressure-sensitive papers. Examples of developers are the clay minerals and phenolic resins already mentioned, or phenolic compounds such as are described, for example, in German Patent Specification 1,251,348, for example 4-tert-butylphenol, 4-phenylphenol, methylenebis(p-phenylphenol), 4-hydroxydiphenyl ether, α-naphthol, β-naphthol, methyl or benzyl 4-hydroxybenzoate, 4-hydroxydiphenyl sulfone, 2,4-dihydroxydiphenyl sulfone, 4'-hydroxy-4-methyldiphenyl sulfone, 4'-hydroxy-4-isopropoxydiphenyl sulfone, 4-hydroxyacetophenone, 2,2'-dihydroxybiphenyl, 4,4'-cyclohexylidenediphenol, 4,4'-isopropylidinediphenol, 4,4'-isopropylidenebis-(2-methylphenol), an antipyrine complex of zinc thiocyanate, a pyridine complex of zinc thiocyanate, 4,4-bis-(4-hydroxyphenyl)-valeric acid, hydroquinone, pyrogallol, phloroglucinol, p-, m- or o-hydroxybenzoic acid, gallic acid, 1-hydroxy-2-naphthoic acid and boric acid or organic, preferably aliphatic, dicarboxylic acids, for example tartaric acid, oxalic acid, maleic acid, citric acid, citraconic acid or succinic acid.

Fusible, film-forming binders are preferably used for the preparation of the heat-reactive recording material. These binders are normally water-soluble, whereas the lactone compounds and the developer are sparingly soluble or insoluble in water. The binder should be capable of dispersing and fixing the colour former and the developer at room temperature.

Under the action of heat the binder softens or melts, so that the colour former comes into contact with the developer and a colour can be formed. Examples of binders which are soluble or at least swellable in water are hydrophilic polymers, such as polyvinyl alcohol, polyacrylic acid, hydroxyethylcellulose, methylcellulose, carboxymethylcellulose, polyacrylamide, polyvinylpyrrolidone, carboxylated butadiene/styrene copolymers, gelatine, starch or etherified maize starch.

If the colour former and the developer are present in two separate layers, it is possible to use binders insoluble in water, i.e. binders soluble in non-polar or only weakly polar solvents, for example natural rubber, synthetic rubber, chlorinated rubber, polystyrene, styrene/butadiene copolymers, polymethylacrylates, ethylcellulose, nitrocellulose and polyvinylcarbazole. However, the preferred arrangement is one in which the colour former and the developer are present in one layer in a water-soluble binder.

The heat-reactive layers can contain further additives. In order to improve the degree of whiteness, to facilitate the printing of the papers and to prevent the heated pen from sticking, it is possible for these layers to contain, for example, talc, titanium dioxide, zinc oxide, aluminium hydroxide, calcium carbonate (for example chalk), clays or organic pigments, for example urea-formaldehyde polymers. In order to ensure that the colour is only formed within a limited temperature range, it is possible to add substances, such as urea, thiourea, diphenylthiourea, acetamide, acetanilide, benzenesulfanilide, bis-stearoylethylenediamide, stearamide, phthalic anhydride, metal stearates, for example zinc stearate, phthalonitrile, dimethyl terephthalate or other appropriate fusible products, which induce a simultaneous melting of the colour former and the developer. Thermographic recording materials preferably contain waxes, for example carnauba wax, montan wax, paraffin wax, polyethylene wax, condensates of higher fatty acid amides and formaldehydes and condensates of higher fatty acids and ethylenediamine.

A further application of the compounds of the formulae (1) to (3) is the preparation of a colour image by means of photo-curable microcapsules, such as are described, for example, in German Offenlegungsschrift 3,247,488.

In the following examples the percentages indicated are by weight, unless stated otherwise. Parts are parts by weight.

EXAMPLE 1

54.3 g of potassium hydroxide and 54.7 g of fluorescein are dissolved successively in 110 g of water. 149.2 g of isopentyl bromide and 3 g of tetrabutylammonium bromide are then also dissolved in the solution. This solution is heated to reflux temperature and is kept at reflux temperature for 22 hours. 200 g of toluene and 80 g of water are then added to the reaction mixture and it is kept at reflux temperature for 30 minutes. The phases are separated. The toluene phase is washed with water and dried with sodium sulfate, after which the toluene is removed by distillation under reduced pressure.

41.1 g of the fluorane compound of the formula

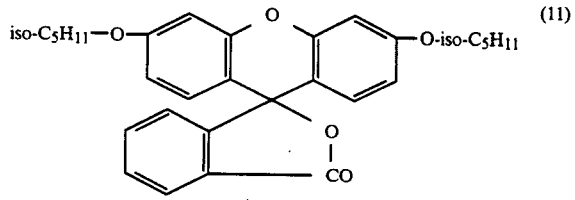

(11)

are obtained in the form of white crystals after recrystallization from isopropanol. The melting point is 126°–128° C. On acid clay this fluorane compound immediately produces an intense yellow coloration, fast to light.

EXAMPLE 2

If the procedure described in Example 1 is repeated, using an equivalent amount of sec-butyl bromide instead of isopentyl bromide, a fluorane compound of the formula

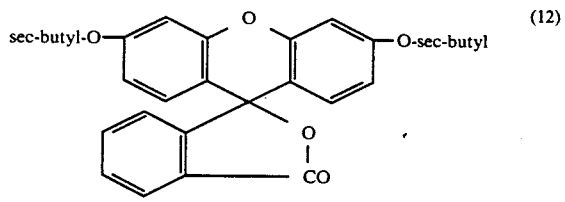

(12)

having a melting point of 65°–70° C. is obtained.

On acid clay this fluorane compound immediately produces an intense yellow coloration.

EXAMPLE 3

(a) 11.2 g of potassium hydroxide and 16.6 g of fluorescein are dissolved successively in 26 g of water. 13.7 g of n-butyl bromide and 0.3 g of tetrabutylammonium bromide are then added. The solution is heated to reflux temperature and is kept at this temperature for 2 hours. The reaction product is isolated as described in Example 1. 4.75 g of an orange compound of the formula

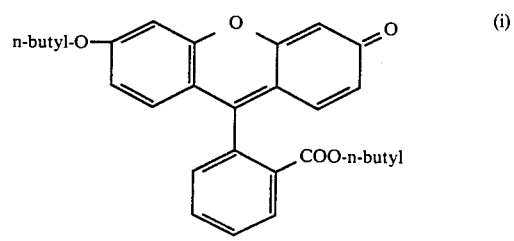

(i)

are obtained. After recrystallization from isopropanol this compound has a melting point of 118°–120° C.

(b) 4.3 g of potassium hydroxide and 4.75 g of the compound of the formula (i) are dissolved successively in 7.3 g of water, after which 8.6 g of n-octyl bromide and 0.07 g of tetrabutylammonium bromide are added. This solution is heated to reflux temperature and is kept at this temperature for 22 hours. 200 g of toluene and 80 g of water are then added to the reaction mixture and it is kept at reflux temperature for 30 minutes. The phases are separated. The toluene phase is washed with water and dried with sodium sulfate, after which the toluene is removed by distillation under reduced pressure.

3.2 g of an unsymmetrically substituted fluorane compound of the formula

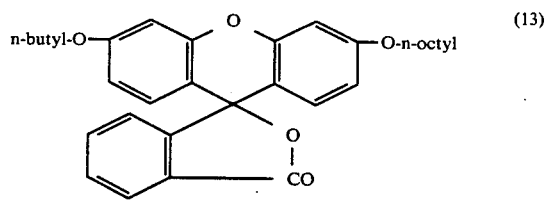

(13)

are obtained.

EXAMPLE 4

22.4 g of potassium hydroxide and 16.6 g of fluorescein are dissolved successively in 548 g of water. 12.3 g of n-propyl bromide, 13.7 g of n-butyl bromide and 0.3 g of tetrabutylammonium bromide are then also dissolved in the solution. This solution is heated to reflux temperature and is kept at reflux temperature for 22 hours. 200 g of toluene and 80 g of water are then added to the reaction mixture and it is kept at reflux temperature for 30 minutes. The phases are separated. The toluene phase is washed with water and dried with sodium sulfate, after which the toluene is removed by distillation under reduced pressure.

This gives 11.5 g of a mixture which, according to HPLC analysis, consists of the fluorane compounds (a) 3,6-di-n-propoxyfluorane, (b) 3-n-butoxy-3-n-propoxyfluorane and (c) 3,6-di-n-butoxyfluorane, the ratio of ((a):(b):(c)) by weight being 1:2:1.

This mixture develops an intense yellow colour on acid clay.

EXAMPLE 5

98.2 g of potassium hydroxide and 83 g of fluorescein are dissolved successively in 231 g of water. 226.6 g of isopentyl bromide and 4.8 g of tetrabutylammonium bromide are then also dissolved in the solution. This solution is heated to reflux temperature and is kept at reflux temperature for 24 hours. 200 g of toluene and 80 g of water are then added to the reaction mixture and it is kept at reflux temperature for 30 minutes. The phases are separated. The toluene phase is washed with water and dried with sodium sulfate, after which the toluene is removed by distillation under reduced pressure.

58.7 g of the fluorane compound of the formula (11) are obtained in the form of white crystals after recrystallization from isopropanol. The melting point is 129°–130° C. On acid clay this fluorane compound immediately produces an intense yellow coloration, fast to light.

EXAMPLE 6

39.2 g of potassium hydroxide and 33.2 g of fluorescein are dissolved successively in 92.4 g of water. 82.2 g of sec-butyl bromide and 1.9 g of tetrabutylammonium bromide are then also dissolved in the solution. This solution is heated to reflux temperature and is kept at reflux temperature for 22 hours. 200 g of toluene and 80 g of water are then added to the reaction mixture and it is kept at reflux temperature for 30 minutes. The precipitate is filtered off. After drying, 20 g of the compound of the formula

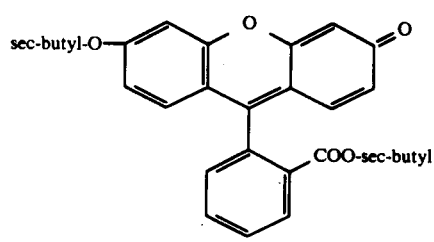

(ii)

are obtained, melting point 134°–137° C.

The phases of the filtrate are separated. The toluene phase is washed with water and dried with sodium sulfate, after which the toluene is removed by distillation under reduced pressure.

Recrystallization from isopropanol gives 6.2 g of the fluorane compound of the formula (12) in the form of amorphous, pale brown plates. The melting point is 50°–60° C. On acid clay this fluorane compound immediately produces a yellow coloration.

EXAMPLE 7

98.2 g of potassium hydroxide and 83.0 g of fluorescein are dissolved successively in 110 g of water. 222.6 g of n-bromopentane and 4.8 g of tetrabutylammonium bromide are then also dissolved in the solution. This solution is heated to reflux temperature and is kept at reflux temperature for 22 hours. 200 g of toluene and 80 g of water are then added to the reaction mixture and it is kept at reflux temperature for 30 minutes. The phases are separated. The toluene phase is washed with water and dried with sodium sulfate, after which the toluene is removed by distillation under reduced pressure.

Recrystallization from isopropanol gives 46.0 g of the fluorane compound of the formula

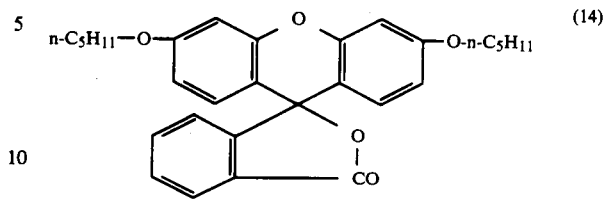

(14)

in the form of white crystals. The melting point is 112°–113° C. On acid clay this fluorane compound immediately produces an intense yellow coloration, fast to light.

EXAMPLE 8

5.8 g of potassium hydroxide and 11.1 g of the compound of the formula (ii) are dissolved successively in 11.5 g of water. 11.9 g of isopentyl bromide and 0.5 g of tetrabutylammonium bromide are then added. The solution is heated to reflux temperature and is kept at this temperature for 24 hours. 100 g of toluene and 40 g of water are then added to the reaction mixture and it is kept at reflux temperature for 30 minutes. The phases are separated. The toluene phase is washed with water and dried with sodium sulfate, after which the toluene is removed by distillation under reduced pressure.

Recrystallization from isopropanol gives 4.9 g of the unsymmetrically substituted fluorane compound of the formula

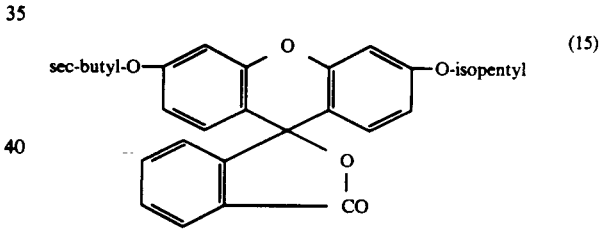

(15)

EXAMPLE 9

115.5 g of potassium hydroxide and 83 g of fluorescein are dissolved successively in 231 g of water. 92.2 g of n-propyl bromide, 102.8 g of n-butyl bromide and 4.8 g of tetrabutylammonium bromide are then also dissolved in the solution. This solution is heated to reflux temperature and kept at reflux temperature for 22 hours. 200 g of toluene and 80 g of water are then added to the reaction mixture and it is kept at reflux temperature for 30 minutes. The phases are separated. The toluene phase is washed with water and dried with sodium sulfate, after which the toluene is removed by distillation under reduced pressure.

This gives 127.15 g of a mixture which, according to HPLC analysis, consists of the fluorane compounds (a) 3,6-di-n-propoxyfluorane, (b) 3-n-butoxy-3-n-propoxyfluorane and (c) 3,6-di-n-butoxyfluorane, the ratio of ((a):(b):(c)) by weight being 1:2:1.

After purification the mixture contains 54.7 g of white crystals of melting point 103°–105° C.

This mixture develops an intense yellow coloration on acid clay.

EXAMPLE 10 a) 49.8 g of fluorescein, 18.6 g of dimethyl methanephosphonate and 34.55 g of potassium carbonate are heated at 100° C. for 3 hours. 300 ml of water are then added. The precipitate is then filtered off and dried. 51.3 g of a compound of the formula

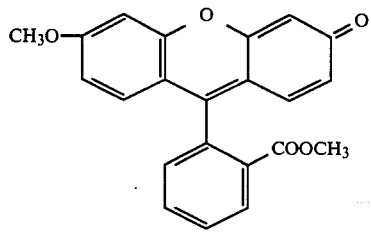
(iii)

are obtained, melting point 207°–211° C.

b) 32.89 g of potassium hydroxide and 51.3 g of the compound of the formula (iii) are dissolved successively in 65.8 g of water. 58.5 g of n-butyl bromide and 2.75 g of tetrabutylammonium bromide are then dissolved in the solution.

This solution is heated to reflux temperature and is kept at reflux temperature for 24 hours. 200 g of toluene and 80 g of water are then added to the reaction mixture, which is kept at reflux temperature for 30 minutes. The phases are separated. The toluene phase is washed with water and dried with sodium sulfate, after which the toluene is removed by distillation under reduced pressure.

Recrystallization from isopropanol gives 23.7 g of the fluorane compound of the formula

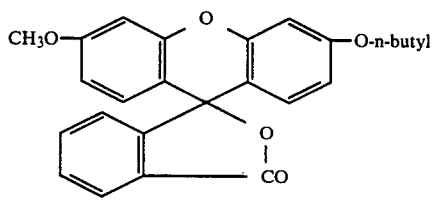
(16)

in the form of pale yellow crystals. The melting point is 129°–131° C.

EXAMPLE 11 a) 3.32 g of fluorescein, 2.74 g of n-butyl bromide, 8.3 g of potassium carbonate, 50 ml of acetone and 0.19 g of tetrabutylammonium bromide are heated under reflux for 17 hours, after which the residue is filtered off and the acetone is removed. This gives 2.74 g of the compound of the formula (i), which, after treatment with hexane, has a melting point of 120°–124° C.

b) 11.1 g of the compound of the formula (i) prepared in accordance with (a) and 5.78 g of potassium hydroxide are dissolved successively in 11.55 g of water. 11.3 g of n-pentyl bromide and 0.48 g of tetrabutylammonium bromide are then dissolved in the solution.

This solution is heated to reflux temperature and is kept at reflux temperature for 20 hours. 100 g of toluene and 40 g of water are then added to the reaction mixture and it is kept at reflux temperature for 30 minutes. The phases are separated. The toluene phase is washed with water and dried with sodium sulfate, after which the toluene is removed by distillation under reduced pressure.

Recrystallization from isopropanol gives 6.1 g of the fluorane compound of the formula

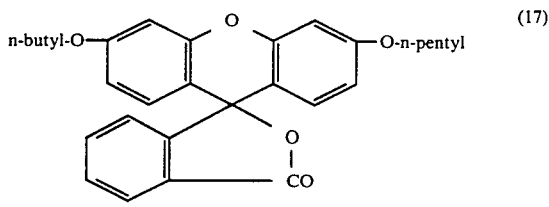
(17)

The melting point is 108°–109°.

EXAMPLE 12

11.1 g of the compound of the formula (i) prepared in accordance with Example 11 (a) and 5.78 g of potassium hydroxide are dissolved successively in 11.55 g of water. 11.92 g of 2-pentyl bromide and 0.48 g of tetrabutylammonium bromide are then dissolved in the solution. This solution is heated to reflux temperature and is kept at reflux temperature for 20 hours. 100 g of toluene and 40 g of water are then added to the reaction mixture and it is kept at reflux temperature for 30 minutes. The phases are separated. The toluene phase is washed with water and dried with sodium sulfate, after which the toluene is removed by distillation under reduced pressure.

Recrystallization from isopropanol gives 3.47 g of the fluorane compound of the formula

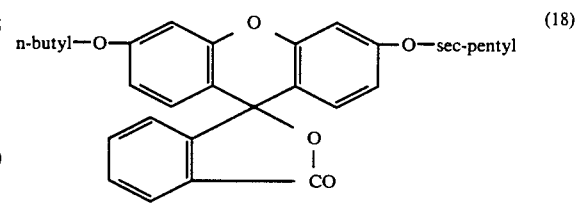
(18)

The melting point is 47°–51° C.

EXAMPLE 13

Preparation of a pressure-sensitive copying paper

A solution of 3 g of the lactone compound of the formula (11) in 80 g of diisopropylnaphthalene and 17 g of kerosene is encapsulated by coacervation with gelatine and gum arabic in a manner known per se, and the product is mixed with starch solution and used to coat a sheet of paper. A second sheet of paper is coated on the front side with acid-activated bentonite as colour developer. The first sheet, containing the colour former, and the paper coated with colour developer are laid on top of one another with the coatings adjacent. Pressure is exerted on the first sheet by writing with the hand or with a typewriter, and an intense yellow copy, which is excellently fast to sublimation and light, immediately develops on the sheet coated with the developer.

Corresponding intense copies, fast to sublimation and light, are also achieved when the colour formers according to Examples 2 to 12 are used.

EXAMPLE 14

The procedure described in Example 13 is repeated, replacing the lactone compound of the formula (11) by a mixture of the following composition: 1.2 g of 3,3-bis-(4′-dimethylaminophenyl)-6-dimethylaminophthalide, 1,2 g of N-butylcarbazol-3-yl-bis-(4′-N-methyl-N-phenylaminophenyl)-methane, 1.2 g of the lactone compound of the formula (11) and 0.4 g of 3,3-bis-(N-octyl-2′-methylindol-3′-yl)-phthalide. A pressure-sensitive recording material which gives an intense black copy, fast to light, as a result of writing with the hand or with a typewriter, is obtained.

EXAMPLE 15

1 g of the lactone compound of the formula (12) according to Example 2 is dissolved in 17 g of toluene. 12 g of polyvinyl acetate, 8 g of calcium carbonate and 2 g of titanium dioxide are added to this solution with stirring. The resulting suspension is diluted with toluene in a 1:1 weight ratio and is used to coat a sheet of paper with a 10 μm doctor blade. A second sheet of paper, the underside of which has been coated at a coating weight of 3 g/m² with a mixture consisting of 1 part of an amide wax, 1 part of a stearin wax and 1 part of zinc chloride, is laid on top of this sheet of paper. Pressure is exerted on the upper sheet by writing with the hand or with a typewriter, and an intense yellow colour, fast to sublimation and light, develops immediately on the sheet coated with the colour former.

EXAMPLE 16

Preparation of a heat-sensitive recording material 32 g of 4,4′-isopropylidene diphenol (bisphenol A), 3.8 g of the distearylamide of ethylenediamine, 39 g of kaolin, 20 g of an 88% hydrolyzed polyvinyl alcohol and 500 ml of water are ground in a ball mill until the particle size is approx. 5 μm. 6 g of the lactone compound of the formula (11), 3 g of an 88% hydrolyzed polyvinyl alcohol and 60 ml of water are ground in a second ball mill to a particle size of approx. 3 μm.

The two dispersions are combined and are used to coat paper at a dry coating weight of 5.5 g/m². An intense orange colour which has excellent fastness to sublimation and light is obtained by touching the paper with a heated metal spike.

Intense and light-fast colours are also obtained if the colour formers according to Examples 2 to 12 are used.

What is claimed is:

1. An etherified fluorescein compound of the formula

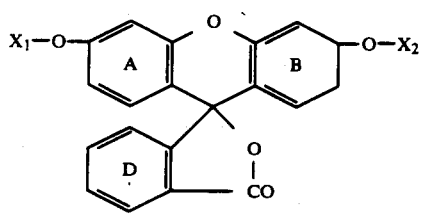

(1)

in which $X_1$ is alkyl having 4 to 12 carbon atoms or $C_5$–$C_6$cycloalkyl and $X_2$ is alkyl having 1 to 12 carbon atoms, which is unsubstituted or substituted by halogen, hydroxyl, cyano or lower alkoxy, or $C_5$–$C_6$cycloalkyl, the rings A and B, independently of one another, are unsubstituted or substituted by 1 or 2 halogen atoms and the ring D is unsubstituted or substituted by halogen, nitro, lower alkyl, lower alkoxy, lower alkylthio, lower alkoxycarbonyl, amino, mono-lower alkylamino or di-lower alkylamino, with the proviso that if one of $X_1$ or $X_2$ is n-butyl, the other cannot be $C_4$-alkyl.

2. A compound according to claim 1 wherein, in formula (1), $X_1$ is n-butyl, isobutyl, sec-butyl, 1,1,3,3-tetramethylbutyl, n-pentyl, isopentyl, n-hexyl or n-octyl and $X_2$ is $C_1$–$C_8$alkyl, 2-cyanoethyl, 2-methoxyethyl or 2-ethoxyethyl.

3. A compound according to claim 1, wherein, in formula (1), the ring D is unsubstituted.

4. A compound according to claim 1, wherein, in formula (1), the rings A and B are unsubstituted.

5. A compound according to claim 2, wherein, in formula (1), $X_2$ is methyl, ethyl, n-propyl, isopropyl, n-butyl, sec-butyl, 1,1,3,3-tetramethylbutyl, isopentyl or n-octyl.

6. A compound according to claim 1, which has the formula

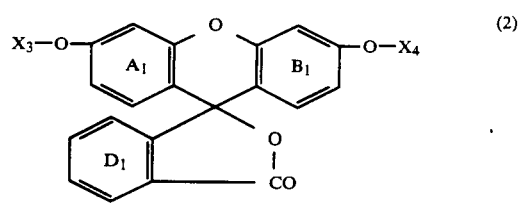

(2)

in which $X_3$ is $C_4$–$C_8$alkyl and $X_4$ is $C_1$–$C_8$alkyl or $C_2$–$C_4$alkyl which is substituted by halogen, cyano or lower alkoxy, and the rings $A_1$, $B_1$ and $D_1$, independently of one another, are unsubstituted or substituted by halogen.

7. A compound according to claim 6, wherein, in formula (2), $X_4$ is $C_1$–$C_5$alkyl and the rings $A_1$, $B_1$ and $D_1$ are unsubstituted.

8. A compound according to claim 1, which has the formula

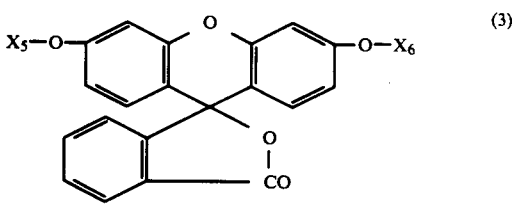

(3)

in which $X_5$ is n-butyl, sec-butyl, isobutyl, n-pentyl, isopentyl, hexyl or n-octyl and $X_6$ is methyl, ethyl, n-propyl, isopropyl, n-butyl, sec-butyl, n-pentyl or isopentyl.

9. A compound according to claim 8, wherein, in formula (3), $X_5$ and $X_6$ are iso-pentyl.

10. A compound according to claim 8, wherein, in formula (3), $X_5$ and $X_6$ are sec-butyl.

11. A compound according to claim 8, wherein, in formula (3), $X_5$ is n-octyl and $X_6$ is n-butyl.

12. A compound according to claim 8, wherein, in formula (3), $X_5$ is n-butyl and $X_6$ is isopentyl.

13. A compound according to claim 8, wherein, in formula (3), $X_5$ is sec-butyl and $X_6$ is isopentyl.

14. A compound according to claim 8, wherein, in formula (3), $X_5$ is n-pentyl and $X_6$ is n-butyl.

15. A mixture comprising 2 or more etherified fluorescein compounds of the formula

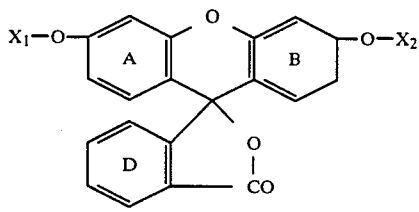

(1)

in which $X_1$ is alkyl having 4 to 12 carbon atoms or $C_5$–$C_6$cycloalkyl and $X_2$ is alkyl having 1 to 12 carbon atoms, which is unsubstituted or substituted by halogen, hydroxyl, cyano or lower alkoxy, or $C_5$–$C_6$cycloalkyl, the rings A and B, independently of one another, are unsubstituted or substituted by 1 or 2 halogen atoms and the ring D is unsubstituted or substituted by halogen, nitro, lower alkyl, lower alkoxy, lower alkylthio, lower alkoxycarbonyl, amino, mono-lower alkylamino or di-lower alkylamino, with the proviso that if one of $X_1$ and $X_2$ is n-butyl, the other cannot be $C_4$-alkyl.

* * * * *